United States Patent [19]

Leonard

[11] Patent Number: 5,495,941

[45] Date of Patent: Mar. 5, 1996

[54] DUAL COMPARTMENT STERILIZABLE WASTE CONTAINMENT UNIT

[75] Inventor: Jeremy W. Leonard, Dallas, Tex.

[73] Assignee: Roatan Medical Services Corporation, Dallas, Tex.

[21] Appl. No.: 224,812

[22] Filed: Apr. 8, 1994

[51] Int. Cl.⁶ ................................................. B65D 85/24
[52] U.S. Cl. ........................... 206/366; 206/370; 220/254; 220/909
[58] Field of Search .................................. 206/366, 370; 220/254, 505, 555, 909

[56] References Cited

U.S. PATENT DOCUMENTS

| | | | |
|---|---|---|---|
| 4,262,802 | 4/1981 | Laauwe | 220/254 |
| 4,729,489 | 3/1988 | Papaianni | 220/555 |
| 4,905,853 | 3/1990 | Stauder | 220/909 |
| 4,991,737 | 2/1991 | Edelman | 220/254 |
| 5,046,613 | 1/1992 | Baudry | 206/366 |
| 5,080,251 | 1/1992 | Noack | 220/335 |
| 5,085,338 | 2/1992 | Inagaki et al. | 220/254 |
| 5,092,462 | 3/1992 | Sagstetter et al. | 206/366 |
| 5,097,950 | 3/1992 | Weiss et al. | 206/366 |
| 5,107,990 | 4/1992 | Wicherski et al. | 206/366 |
| 5,111,951 | 5/1992 | Breen et al. | 220/909 |
| 5,165,564 | 11/1992 | Prout et al. | 220/254 |
| 5,249,680 | 10/1993 | Shillington | 206/366 |
| 5,277,312 | 1/1994 | Vumbaca | 206/366 |
| 5,323,902 | 6/1994 | Palmer et al. | 206/366 |
| 5,392,916 | 2/1995 | Paulison | 220/909 |

*Primary Examiner*—David T. Fidei
*Attorney, Agent, or Firm*—Harris, Tucker & Hardin

[57] ABSTRACT

A reusable dual compartment sterilizable waste containment unit has a rigid walled container divided into a large soft waste cavity and a smaller sharp waste compartment in a single unitary container. The mouths of the cavity and the compartment are located at and circumscribed by a rim of the walled container which supports a removable closure and cover. The closure has a large opening leading to the mouth of the cavity and a smaller opening leading to the mouth of the compartment to facilitate use of the same waste containment unit for both kinds of infectious waste which are collected and stored separately. The cover has a port leading to the interior which permits access to the soft waste cavity when the lid is unlifted. The port is useful to introduce water and/or steam into the interior. The waste containment unit is molded from plastic which can withstand repeated exposure to steam produced from water in the unit by high energy microwave radiation. The lid is hingedly connected to the closure for lifting to expose the opening to the interior. The subassemblies are nestable and stackable and adapted for reuse by sterilization of the contents in the container. After sterilization, the contents may be safely shredded and disposed of in the ordinary waste stream and the article reused.

30 Claims, 3 Drawing Sheets

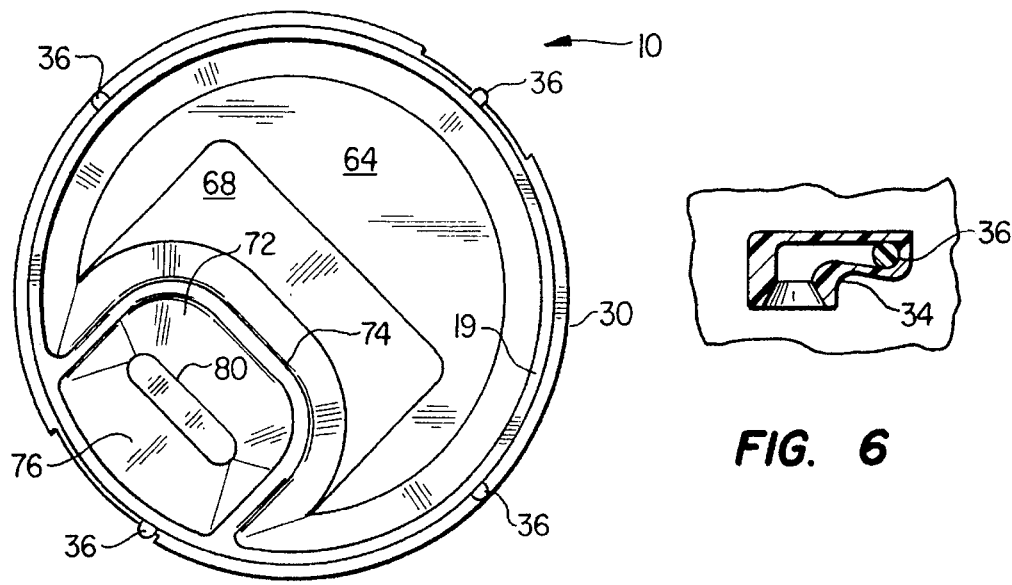
FIG. 2
FIG. 6
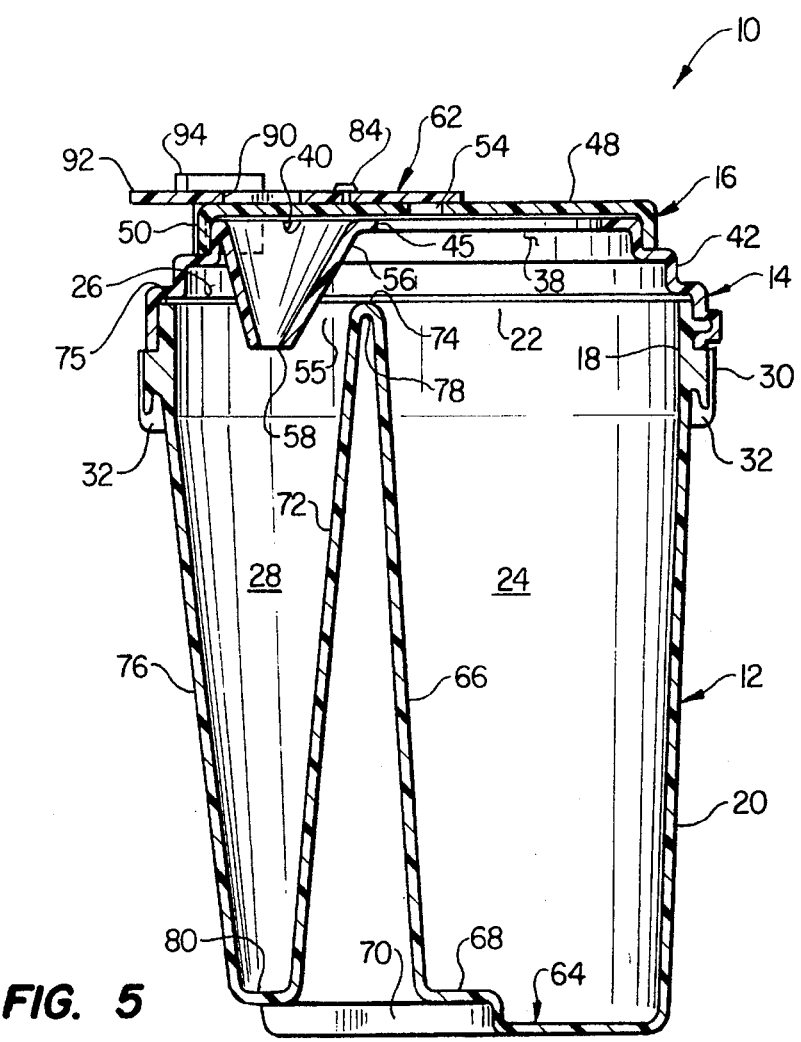
FIG. 5

DUAL COMPARTMENT STERILIZABLE WASTE CONTAINMENT UNIT

TECHNICAL FIELD OF THE INVENTION

The invention relates generally to medical waste collection, storage and disposal, and in particular, discloses a reusable dual compartment unit which handles soft waste separately from sharp waste.

BACKGROUND OF THE INVENTION

There is an ever-increasing awareness in the medical and hospital industry of the need to safely containerize, transport and dispose of infectious medical waste. The fear of contamination from contact with infectious bodily fluids has become a great concern to all.

Infectious medical waste may be considered as comprising two primary categories related to its physical characteristics. The soft waste category may be characterized by such things as masks, gloves, bandages, pillows, cotton products, in general, anything which is not "sharp." The sharp waste category is characterized by such things as needles, syringes, scalpel blades, glass or broken glass, in general, things which present edges which can puncture or cut.

The most common current practices for collection and disposal of infectious medical waste are rather crude and require the separate disposal of sharp waste and soft waste. It is believed that over 90% of the hospitals and doctor offices that currently generate infectious medical waste dispose of the soft waste in a fiberboard box lined with a red trash bag which serves to contain some of the liquids that are disposed of. Waste is thrown into the box/bag until the box is full. The flaps at the top of the box are folded over and taped shut. The box is then transported for incineration at another location. One major disadvantage with the use of the box and bag is that the system allows liquids to soak through the box, contaminating the work area. Although the plastic bag is a barrier if it remains intact, all plastic bags can leak with only the smallest of punctures. This can easily occur due to the presence of improperly disposed of sharp waste that gets mixed in with the soft waste. This can easily puncture the sides of the cardboard box and injure workers. In addition, the waste is exposed to the air until the box is closed and hauled away, which can be days or weeks. Another big disadvantage is the expense of using the box and bag only once. They are usually incinerated, together with the contents.

Sharp waste is currently disposed of in puncture-proof, disposable plastic containers which are sized anywhere from one quart to five gallons. While these containers do an adequate job of containerizing the sharp waste, they are also designed to be disposable and, therefore, expensive. It is estimated that an average hospital will spend almost $200 per bed per year on these sharp waste containers.

Some hospitals have experimented with reusable medical waste disposal containers, which are nothing more than large plastic trash cans with lids. These containers are meant to transport waste through the hospital to an incinerator or other point of disposal. Once the containers have arrived at their destination, the contents must be dumped out, which increases the chance of workers coming into contact with infectious waste. After these containers have been used, they must be cleaned and disinfected in some manner.

It must be recognized that the soft waste and sharp waste are frequently generated at the same location. Bandages are removed and injections given at the same location. It would be desirable to have a unit to contain and receive both types of waste. Such a unit should facilitate the separation of the two types of waste without interfering one with the other. It should be designed to accept bulky soft waste in a large compartment and sharp waste in a smaller compartment, while keeping the two kinds of waste separate. Cost considerations dictate that the unit used for collection, containment and transport should be safely reusable. The unit should be transportable without danger of losing the contents if overturned during normal operations, and should be treatable in some manner for reuse without reintroducing infectious agents into the patient areas. The contained waste and the containment unit are preferably sterilizable by application of heat energy and/or steam. The unit should be nestable and stackable to conserve valuable medical storage space. The invention described herein meets these criteria and more.

SUMMARY OF THE INVENTION

The invention may be described as a reusable article which is a dual compartment container for collecting and safely containing mixed medical waste which can be transported safely to a sterilizing facility to be sterilized in the container. The container has a relatively large internal soft waste cavity and a smaller sharp waste compartment which are separated by puncture-proof walls from each other. A liftable cover is positioned over openings leading to the soft waste cavity and the separate sharp waste compartment. The cover is mounted on the container so that it is normally in the unlifted position. In the unlifted position of the cover, the cover has a wall which blocks access to the interior of the container. The cover has a port which can be uncovered after the containment unit is transported to a sterilization station in order to introduce water or steam into the soft waste cavity, and via internal passages, into the sharp waste container, as well.

When the cover is unlifted, no waste can be deposited in the separate sharp waste compartment or the soft waste cavity. In order to dispose of soft waste in the soft waste cavity, it is only necessary to lift the cover. Because the medical worker has to lift the cover to deposit soft waste or sharp waste, there is little or no tendency of inadvertently depositing sharp waste in with soft waste. The sharp waste is deposited in a separate walled compartment in the dual containment unit. This avoids an important problem that occurs when workers attempt to push the bulky soft waste down by hand in order to add additional material to the container. It is easy to see that contamination of the soft waste with needles or syringes could result in "needle sticks." The design of the article makes it possible to provide a single dual compartment container which is safer, occupies less floor space, and offers a single place for disposal as opposed to several places if separate containers are used for each kind of waste.

More particularly, the reusable article, which is a container for collecting and safely containing mixed medical waste to be sterilized in the container, comprises a walled container having an upper perimeter rim defining the mouths of a soft waste cavity and a sharp waste compartment in the container, both of the mouths being encompassed within the rim area for separately collecting and containing soft waste and sharp waste. A closure removably mounted on the rim has a large opening leading in the mouth of the soft waste cavity, which is sized to permit easy access for the deposit of soft waste. The closure has a smaller opening leading to the mouth of the sharp waste compartment, at the same elevation as the opening for the soft waste cavity. The liftable cover is hingedly mounted on the rim or the closure, having a lifted position which exposes the large opening in the closure for disposal of soft waste into the soft waste cavity and the smaller opening for disposal of sharp waste into the sharp waste compartment. The cover has an unlifted position wherein the cover closes both openings to prevent disposal of waste into the interior of the container. The cover has a port or opening which is preferably positioned over the mouth of the soft waste cavity when the cover is moved to the unlifted position, whereby water or steam may be introduced at a sterilization facility after the container is filled. The mouth of the sharp waste container occupies a lesser portion of the area encompassed by the rim.

The walls of the container are relatively rigid to prevent puncture by sharp objects and provide a free-standing structure. The walled container has a wall forming sides of the soft waste cavity which terminate at a bottom wall which rests on a surface to support the container in an upright position. The wall which forms sides of the soft waste cavity includes an outer wall and an inner wall which extends inwardly toward the center with respect to the rim area, the inner wall providing a space within the confines of a downward projection of the rim circle, the space extending downwardly toward the bottom, in which the sharp waste compartment is mounted for use. The rim defines the mouth of the sharp waste compartment at substantially the same elevation as the mouth of the soft waste cavity. The sharp waste compartment has a separate side wall extending downwardly from its mouth and terminating in a closed bottom, the side wall of the sharp waste compartment merging with the inner wall of the soft waste cavity at a collocated portion of said mouths. The container is preferably molded integrally from suitable molding plastic such that the rim of the walled container circumscribes the mouths of the soft waste cavity and the separate sharp waste compartment and forms a part of the mouth of each.

The opening defined in the closure for the sharp waste compartment has a depending funnel-shaped wall leading to an entry for sharp waste whereby sharp waste deposited into the mouth of the sharp waste compartment is guided into the separate sharp waste compartment via the funnel-shaped wall. The entry formed by the funnel-shaped wall underlie the mouth of the sharp waste compartment and is located at an elevation some distance below the elevation of the perimeter rim of the walled container. The closure may be thought of as like a lid which fits over the rim with the center portion cut away over the mouth of the soft waste container and a portion cut away adjacent the outer edge over the sharp waste compartment.

The closure is equipped with a plurality of lugs, and the rim with corresponding pins to removably fix the closure to the rim. The cover is preferably hingedly connected to the closure so that the closure and cover can be removed from the rim as a unit. The article is preferably molded from plastic, having the characteristic of temperature and steam resistance suitable for repeated autoclaving. More particularly, the plastic should be structurally and chemically resistant to steam produced from water added to the interior which is heated and changed to steam by high intensity microwave energy applied to the article. The removable closure makes it convenient to dump the contents and replace the closure and cover for reuse after the entire unit and contents have been sterilized.

The cover is provided with a repositionable locking means capable of simultaneously blocking a port in the cover and locking the cover in the unlifted position. The locking means has a tongue which slides under a catch on the closure to lock the cover. The locking means can be repositioned to unblock the port for access. The cover includes the port or opening for entrance of steam or fluid into the soft waste cavity. The locking means can be rotated to block the port without locking the cover. This is the normal use position. The locking means extends outwardly from the cover to serve as a handle for lifting the cover. The locking means can be rotated to block the port and simultaneously lock the cover for transport to the sterilizing site. Repositioning the locking means once again exposes the port. This allows water or steam to enter the soft waste cavity and via internal passages, the separate sharp waste compartment, to sterilize the contents. Water can be added to the soft waste compartment and vaporized into steam with microwave radiation to sterilize the contents.

BRIEF DESCRIPTION OF THE DRAWINGS

FIG. 2 is a plan view of the container on the lines 2—2 of FIG. 1;

FIG. 5 is a cut-away elevational view of the assembled article on the lines 5—5 of FIG. 4;

FIG. 6 is a cut-away view of one version of a releasable latch used to fix the closure on the rim of the container.

DETAILED DESCRIPTION OF THE INVENTION

Figure 1:
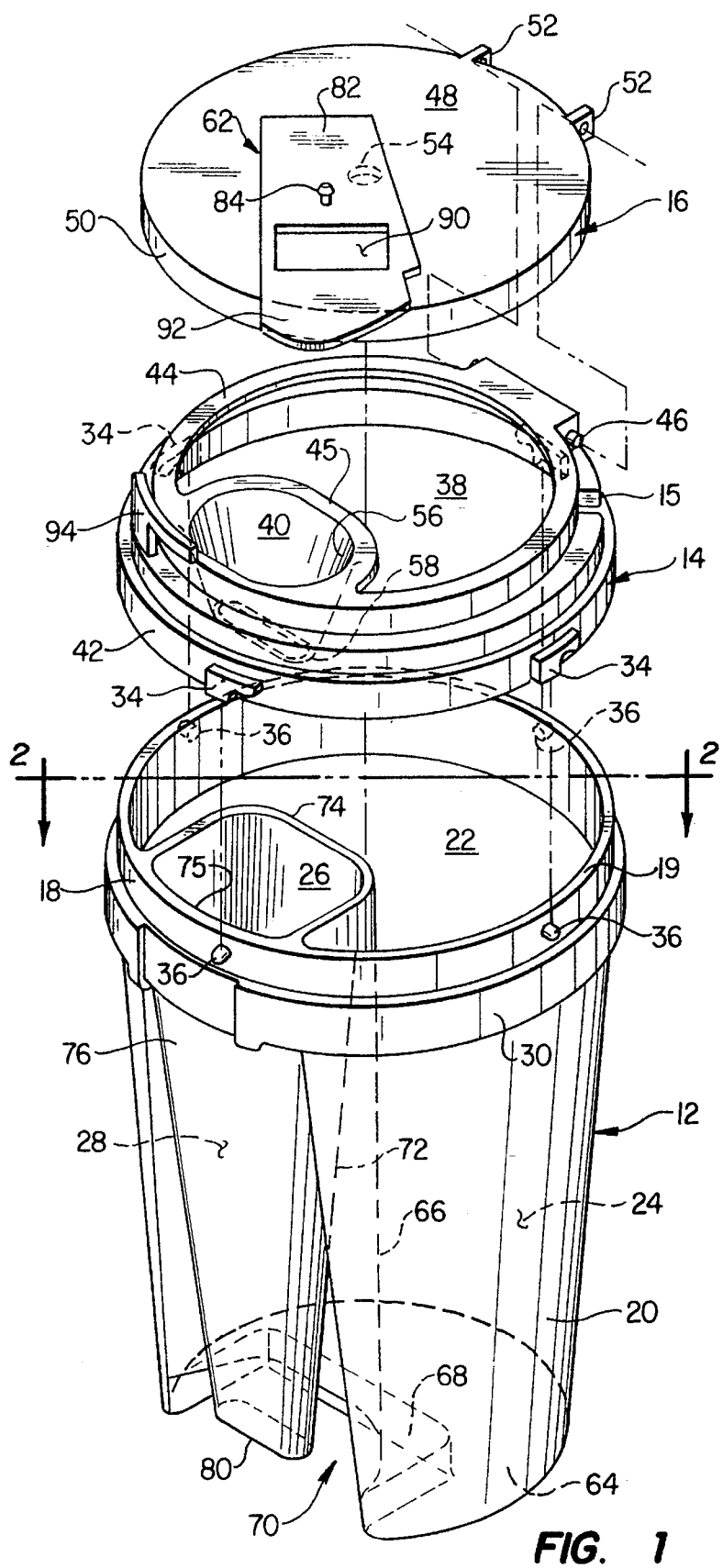
FIG. 1 is an exploded perspective view of the article comprising the container, the closure and the lid.

In FIGS. 1–6, like items are identified by like and corresponding numerals for ease of reference. Referring first to FIG. 1, the article incorporating the preferred embodiment of the present invention is generally identified by reference numeral 10. The article 10 comprises a walled container generally designated by the reference numeral 12, a closure member generally designated by the reference numeral 14, and a cover member generally designated by the reference numeral 16. Walled container 12 has a wall 20 and a rim 18 mounted on the upper portion of wall 20 or integrally formed as rim 18. Rim 18 circumscribes the mouth 22 of a soft waste cavity 24 and the mouth 26 of a separate sharp waste compartment 28. The sharp waste compartment is separated from the soft waste cavity. Its mouth 26 is encompassed within the rim area of rim 18 for collecting and containing sharp waste separately.

Closure 14 is mounted on rim 18 in the manner indicated in FIG. 5. Rim 18 may include a band 30 around its periphery which extends laterally outwardly to provide a finger opening 32 to facilitate lifting the container. Closure 14 fits down over rim 18 and is removably locked in place by a series of cooperating lugs 34 and pins 36 which are shown interlocked in FIG. 6. Any suitable locking means could be used to releasably lock the closure to the rim. Thumb holes 15 may be provided to facilitate unlocking the closure. Closure 14 has a large opening 38 leading to mouth 22 of soft waste cavity 24 which permits easy access for deposit of soft waste. Closure 14 also includes an opening 40 leading to mouth 26 of sharp waste compartment 28. Closure 14 has an irregular peripheral wall 42 which rises upwardly in steps to terminate at a relatively flat upper surface 44 which defines the openings 38 and 40.

An arcuate radially inwardly extending portion 45 of flat surface 44, together with the remainder of upper surface 44, defines opening 40. Depending from upper surface 44 and 45 around opening 40 is a funnel-shaped wall 56 having steeply angled sides leading to an entry 58 into mouth 26 whereby sharp waste is guided into the sharp waste compartment. Entry 58 underlies opening 40 and lies inside mouth 26 below rim 18.

Adjacent upper surface 44 of closure 14 are pivots 46 which may be used to engage a cover member or cover 16. Cover 16 is formed with a flat wall 48 having a circular rim 50 from which extend pivot connections 52 which are engageable with pivots 46 on closure 14 to hingedly connect the cover thereto. Cover 16 is operable between a lifted position which provides access to opening 38 and an unlifted position wherein wall 48 rests on upper surface 44 simultaneously closing openings 38 and 40. Cover 16 has a port 54 which is positioned over opening 38 and mouth 22 in the unlifted position of the cover. Cover 16 includes port 54 for water, steam or other fluid and a locking means generally designated as 62 which will be described more fully in the discussion of FIGS. 3 and 4.

Referring now to FIGS. 1, 2 and 5, the structure of walled container 12 is more fully described. Wall 20 is more properly described as an outer wall forming the sides of the soft waste cavity, extending downwardly from rim 18 and terminating at a bottom wall 64 which rests on a surface to support container 12 in a upright position. Wall 20 is tapered inwardly toward the bottom to permit nesting of multiple containers. The outer wall is generally cylindrical and is preferably integrally formed with rim 18. Wall 20 is formed to include an arcuate radially inwardly extending inner wall 66, which together with bottom 64 and the remainder of wall 20 defines the soft waste cavity 24. Bottom 64 includes a raised ledge 68 which defines a U-shaped cavity 70, generally located under the mouth 26 of the separate sharp waste compartment. The location of cavity 70 may be regarded as the front of the article. Inner wall 66 is arcuately curved inwardly to provide a space within the confines of the rim and extending downwardly to the bottom of the container which allows the sharp waste compartment to be located within the downward projected circle area of the rim 18. The U-shaped cavity is designed to permit stacking of the assembled articles by providing room for locking mechanism 62 when one container is stacked on the cover of another container. Sufficient support is provided by bottom 64 around cavity 70 to support the container in this manner.

Mouth 26 has a perimeter 74 having a part 75 which lies arcuately along the top surface 19 of rim 18. The remainder of perimeter 74 extends radially inwardly from the rim toward the upper center part of the container at about the level of rim 18. The separate compartment is formed by a separate wall 72 which extends downwardly from perimeter 74 of mouth 26, inwardly from the front, and a front wall 76 which merges with rim 18 along the perimeter of the rim. Wall 72 merges at 78 with wall 66 at perimeter 74 in FIG. 5. Walls 72, 76 are tapered inwardly downward to a bottom 80 which is located just above cavity 70 so as to avoid interfering with locking means 62 when containers are stacked. Like walls 20,66, the walls 72,76 of the separate container are tapered for nesting of one container within another container so that a great number of containers can be placed in a given vertical space.

The walls 72 and 76 are, of course, continuous, together with bottom 80 so that the separate compartment 28 can safely segregate and hold sharp waste apart from soft waste cavity 24. Although the preferred unitary structure is shown in FIGS. 1, 2 and 5, the separate compartment could be a separate piece adapted to drop into a supporting rim structure at perimeter 74. It is also possible to merge part of inner wall 66 and compartment wall 72 all or part of the way toward the bottom instead of having two separate walls. The structure shown in FIGS. 1, 2 and 5 or variations thereof are especially adapted to nest because the walls which depend downwardly from rim 18 and perimeter 74 are angled and tapered inwardly and an interior space is provided between sharp waste compartment 28 and soft waste cavity 24.

Figure 4:
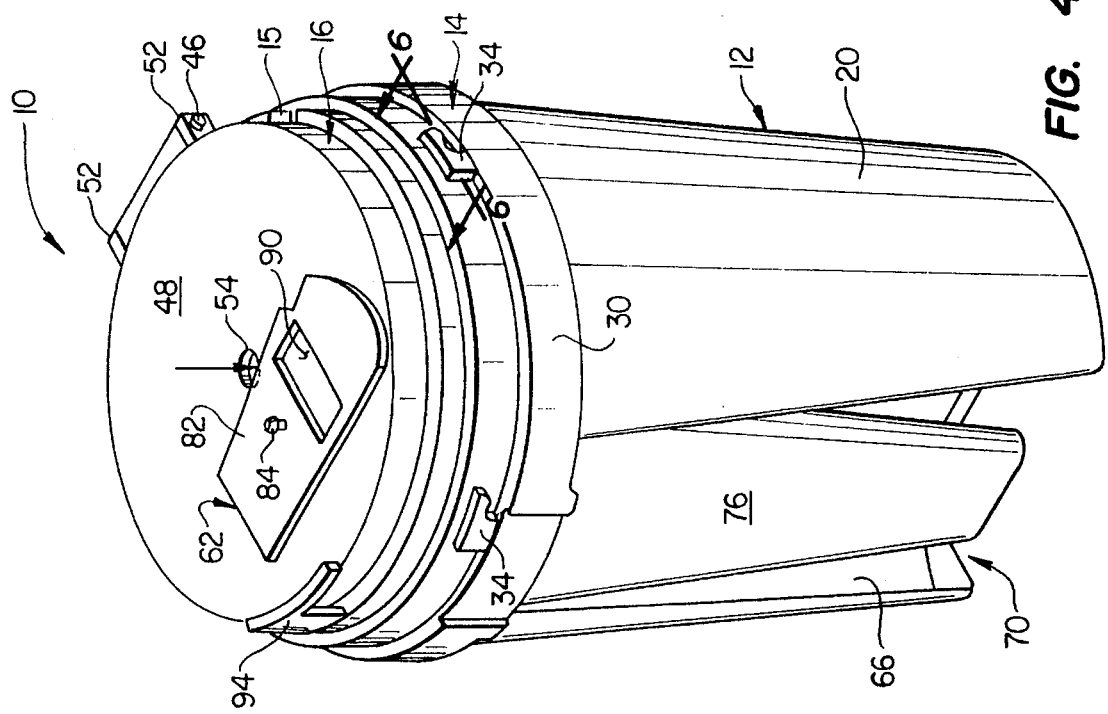
FIG. 4 is a perspective view of the assembled unit of FIG. 3 with the locking means repositioned to expose the port.
Figure 3:
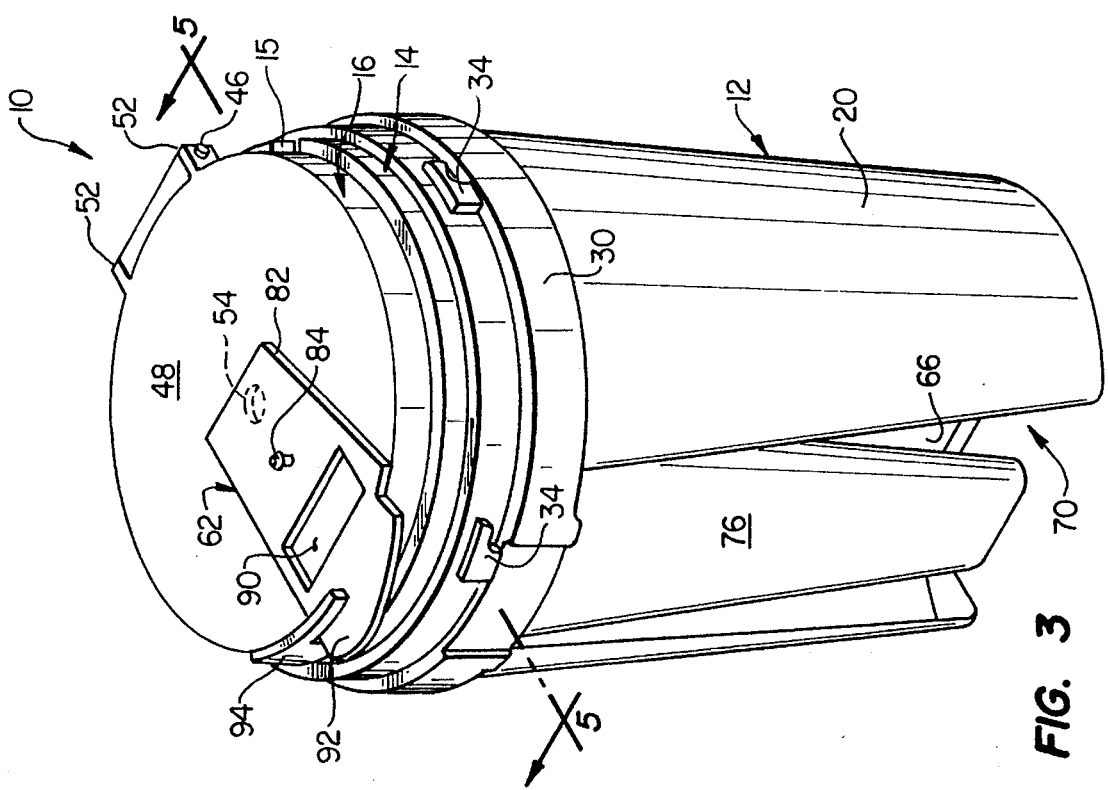
FIG. 3 is a perspective view of the assembled article showing the locking means positioned to block the port in the cover with the cover locked for transport.

Referring now to FIGS. 1, 3 and 4, locking means 62 will be further described. For convenience, it will be referred to as a locking means, although it performs additional sealing functions. A slide 82 is an elongated body mounted at pivot post 84 on cover 16. The slide may be equipped with detents which cooperate with detents on the cover to hold it in several operating positions. It has an opening 90 which cooperates to receive bottom 80 when fully assembled articles 10 are vertically stacked one on another. Locking means 62 includes a tongue 92 on the forward part of slide 82 which is adapted to cooperate with catch 94 mounted in position on the periphery of closure 14 at wall 42.

In FIG. 1, locking means 62 is in the normal use position rotated approximately 90 degrees from the FIG. 4 position on post 84 so that the cover is unlocked. In this position, the cover may be raised or lowered at will by grasping tongue 92. In FIG. 3, locking means 62 has been repositioned by rotating clockwise to lock cover 16 by cooperation of tongue 92 and catch 94 as shown. The rear portion of slide 82 covers port 54. In this position, the article is completely sealed and locked, and the cover may not be opened. This is the transport position whereby the article may be transported to a sterilizing site where steam sterilization may be applied.

In FIG. 4, locking means 62 has been repositioned by rotating on post 84 from a first position of FIG. 1 to a second position as shown, exposing port 54. Opening 54 is exposed whereby water or steam may enter the soft waste compartment through opening 50, and enter the sharp waste compartment via an open passage 55 between funnel-shaped wall 56 and the juncture 78 between walls 66 and 72 best seen in FIG. 5. This is the sterilizing position.

The article which is described herein is a reusable, rigid plastic container that prevents punctures and leaks. The unique dual-chamber design allows both sharp waste and soft waste to be disposed of in the same container without mixing the waste streams. All waste is sterilized within the unit, eliminating double handling of waste. Cost associated with incineration and single use of containers is eliminated. The article is attractive and may be used in a patient's room. No one ever has to touch the waste after it goes into the container. Waste odors are held in. Each of the individual subassemblies comprising the container portion and the combined closure and cover are designed to be nestable with subassemblies of like kind, and the units are designed to be stackable, as well. The unit is sized to provide a capacity of about 4.5 cubic feet of infectious waste. A suitable unit is believed to be about 2 feet high and about 18 inches in diameter. The cover has approximately a one inch diameter opening for steam. These dimensions may be suitably adjusted to meet specific design criteria.

After the unit is filled with infectious waste, it is designed to be transported to a sterilizing chamber, preferably including the injection of water through the steam hole in the cover followed by exposure to microwave energy and/or steam at elevated temperature. The unit is preferably suitable for repeated autoclaving and exposure to microwave energy sufficient to vaporize internal water and create steam. The unit is preferably molded as integral subassemblies comprising the container, the closure member and the cover. It is believed that cross-linked, high density polyethylene or moldable polypropylene are suitable plastics for construction of the article. Although the article has been described in terms of a basically circular cross-section, it should be appreciated that a suitable dual chamber container could be made in a generally square shape or other polygonal shape.

Although the present invention has been described with respect to a specific preferred embodiment thereof, various changes and modifications may be suggested to one skilled in the art, and it is intended that the present invention encompass such changes and modifications as fall within the scope of the appended claims.

I claim:

1. A reusable article for collecting and safely containing mixed medical waste to be sterilized in situ, comprising:

a rigid walled container having a rim circumscribing the mouths of a soft waste cavity and a separate sharp waste compartment;

a removable closure defining an opening for the soft waste cavity and a smaller opening for the sharp waste compartment, said closure being mounted on the rim with the respective openings for the soft waste cavity and the sharp waste compartment leading into said mouths;

a cover mounted on the article above the closure, having a wall placeable to prevent access to the container by blocking said opening for the soft waste cavity and said opening for the sharp waste compartment;

the cover being liftable to access the sharp waste compartment and the soft waste cavity by exposing the opening of said soft waste cavity and said sharp waste compartment leading to said mouths whereby sharp waste can be deposited in said sharp waste compartment or soft waste deposited into said soft waste cavity.

2. The reusable article of claim 1, wherein the cover is provided with a repositional locking means capable of locking said cover in an unlifted position wherein the wall of the cover blocks the openings of the soft waste cavity and the sharp waste compartment.

3. The reusable article of claim 2 wherein said cover contains a port and said locking means is positional to block said port for access while continuing to lock said cover in the unlifted position.

4. The reusable article of claim 2 wherein said cover includes an opening for entrance of steam or liquid into the soft waste cavity, which is blocked by the locking means when the locking means is positioned to lock said cover in the unlifted position.

5. The reusable article of claim 1 wherein said cover is provided with a locking means which rotates to open or close a port and simultaneously lock or unlock said cover.

6. The reusable article of claim 5 wherein said cover is hingedly mounted with said closure for lifting to expose said openings of the soft waste cavity and the sharp waste compartment.

7. The reusable article of claim 2 wherein said cover is hingedly mounted with said closure for lifting to expose said openings of the soft waste cavity and the sharp waste compartment.

8. The reusable article of claim 7 wherein said locking means is repositional on said cover to cooperate with a latch extending from said closure to lock said cover to said closure.

9. The reusable article of claim 7 wherein said article is formed from a plastic material resistant to microwave energy and steam, suitable for repeated autoclaving in the presence of microwave energy at a level that turns water in the article into steam.

10. The reusable article of claim 9 wherein the opening defined in the closure for the sharp waste compartment has a depending funnel-shaped wall leading into the mouth of the sharp waste compartment whereby sharp waste deposited into said opening defined in the closure is guided into the separate sharp waste compartment.

11. The reusable article of claim 1 wherein the opening defined in the closure for the sharp waste compartment has a depending funnel-shaped wall leading into the mouth of the sharp waste compartment whereby sharp waste deposited into said opening is guided into the sharp waste compartment.

12. The reusable article of claim 11 wherein the walled container has walls which are tapered to permit nesting of one walled container in another walled container so that many such walled containers can be stacked in a relatively small space.

13. The reusable article of claim 1 wherein the walled container has walls joined at the elevation of the rim which separately define the sharp waste compartment by providing a space below the rim around said sharp waste compartment thereby promoting nesting of multiple ones of said walled containers for stacking in a relatively small storage space.

14. A reusable article which is a container for collecting and safely containing mixed medical waste to be sterilized in the container, comprising:

a rigid walled container having walls and a perimeter rim containing the mouth of a soft waste cavity and the mouth of a sharp waste compartment, the mouth of the sharp waste compartment being formed by a radially inwardly and downwardly extending wall connected to the perimeter rim and partially defining the mouth of the soft waste, cavity;

a sharp waste compartment defined by said radially inwardly and downwardly extending wall in said container, having its mouth encompassed within said rim area for collecting and containing sharp waste separately;

a closure removably mounted on the rim and having a large opening leading into the mouth of the soft waste cavity, which is sized to permit easy access for the deposit of soft waste;

a liftable cover hingedly mounted on the article, said cover having a lifted position which exposes the large opening in the closure for disposal of soft waste into the soft waste cavity and an unlifted position wherein said cover closes the large opening to prevent disposal of soft waste into said soft waste cavity.

15. The reusable article of claim 14 wherein the walls of the container are tapered and there is a space provided below said rim, separating said sharp waste compartment from said soft waste cavity to permit nesting of multiple containers.

16. The reusable article of claim 15 wherein the mouth of the sharp waste compartment occupies a lesser portion of the area encompassed by said rim and is smaller than the mouth of the soft waste cavity.

17. The reusable article of claim 16 wherein the walled container has a wall forming sides of the soft waste cavity, terminating at a bottom wall which can rest on a surface to support the container in an upright position.

18. The reusable article of claim 17 wherein the wall which forms sides of the soft waste cavity includes an outer wall and an inner wall, the inner wall extending radially inwardly toward the soft waste cavity, within the downward projected area circumscribed by the perimeter rim, said inner wall providing a space under the perimeter rim area extending downwardly toward said bottom, in which said sharp waste compartment is mounted for use.

19. The reusable article of claim 18 wherein said perimeter rim defines the mouth of the sharp waste compartment and the mouth of soft waste cavity at substantially the same elevation.

20. The reusable article of claim 18 wherein said sharp waste compartment has a separate side wall and bottom extending downwardly from its mouth, said side wall of the sharp waste compartment merging with the inner wall of the soft waste cavity at the elevation of the perimeter rim of the walled container, to partially define said mouths.

21. The reusable article of claim 20 wherein said closure, in addition to the opening to the soft waste cavity, defines a smaller opening into the mouth of the sharp waste compartment.

22. The reusable article of claim 21 wherein the opening defined in the closure for the sharp waste compartment has a depending funnel-shaped wall leading to an entry for sharp waste whereby sharp waste deposited into the mouth of the sharp waste compartment is guided into the sharp waste compartment.

23. The reusable article of claim 22 wherein said entry for sharp waste is formed by the funnel shaped walls at an elevation located some distance below the elevation of the perimeter rim of the walled container.

24. The reusable article of claim 21 wherein said cover is provided with a repositional locking means movable to open a port in the cover, and closing the port in the cover with or without locking the cover in the unlifted position.

25. A reusable article which is a container for collecting and safely containing mixed medical waste to be sterilized in the container, comprising:

an upright rigid walled container having an upper perimeter rim defining and circumscribing the mouth of a large soft waste cavity in the container and partially defining the mouth of a smaller sharp waste compartment in the container;

the remainder of the mouth of the smaller sharp waste compartment being defined by a radially inwardly extending wall extending radially inwardly from the upper perimeter rim and extending downwardly from the rim to a bottom to form a separate sharp waste compartment in the container;

a liftable cover hingedly mounted on said article, having an unlifted position over the mouths of the soft waste cavity and the sharp waste compartment, the cover having a wall having a port located over the soft waste cavity;

the unlifted cover preventing access to the soft waste cavity, the soft waste cavity being accessible for disposal of soft waste only when said cover is lifted.

26. The reusable article of claim 25 wherein said walled container is formed by integrally molding in plastic.

27. The reusable article of claim 26 wherein said plastic is selected from moldable plastics having the characteristic of temperature and steam resistance suitable for repeated autoclaving.

28. The reusable article of claim 26 wherein the wall of the container is tapered to permit nesting of multiple containers.

29. The reusable article of claim 28 wherein the walled container has an outer wall forming sides of the soft waste cavity terminating at a bottom wall which rests on a surface to support the container in an upright position;

the outer wall which forms sides of the soft waste cavity being formed to include an inner wall which extends downwardly and radially inwardly toward the center with respect to the downwardly projected rim area, said inner wall providing a space within the confines of the rim area extending downwardly toward said bottom in which said sharp waste compartment is mounted for use.

30. The reusable article of claim 29 wherein said sharp waste compartment has a separate side wall portion extending downwardly from its mouth, said side wall portion of the sharp waste compartment being collocated and merging with the inner wall of the soft waste cavity at said mouths.

* * * * *